US009823586B2

(12) United States Patent
Quintanilha

(10) Patent No.: US 9,823,586 B2
(45) Date of Patent: Nov. 21, 2017

(54) INSPECTION APPARATUS, INSPECTION METHOD AND MANUFACTURING METHOD

(71) Applicant: ASML Netherlands B.V., Veldhoven (NL)

(72) Inventor: Richard Quintanilha, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/230,937

(22) Filed: Aug. 8, 2016

(65) Prior Publication Data

US 2017/0045823 A1    Feb. 16, 2017

(30) Foreign Application Priority Data

Aug. 12, 2015 (EP) .................................. 15180807

(51) Int. Cl.
*G03B 27/68* (2006.01)
*G03F 7/20* (2006.01)
(Continued)

(52) U.S. Cl.
CPC ....... *G03F 7/7065* (2013.01); *G01N 21/4788* (2013.01); *G01N 21/95607* (2013.01);
(Continued)

(58) Field of Classification Search
CPC ............... G03F 7/7065; G03F 7/70633; G03F 7/70483; G03F 7/70683
(Continued)

(56) References Cited

U.S. PATENT DOCUMENTS

| 7,792,246 B2 | 9/2010 | Rodenburg et al. |
| 8,908,910 B2 | 12/2014 | Maiden |

(Continued)

FOREIGN PATENT DOCUMENTS

| DE | 102012022961 A1 | 5/2014 |
| DE | 102012022966 A1 | 5/2014 |

(Continued)

OTHER PUBLICATIONS

International Search Report and Written Opinion of the International Searching Authority directed to Appl. No. PCT/EP2016/068317, dated Nov. 18, 2016; 12 pages.

(Continued)

*Primary Examiner* — Hung Henry Nguyen
(74) *Attorney, Agent, or Firm* — Sterne, Kessler, Goldstein & Fox P.L.L.C.

(57) ABSTRACT

A product structure (407, 330') is formed with defects (360-366). A spot (S) of EUV radiation which is at least partially coherent is provided on the product structure (604) to capture at least one diffraction pattern (606) formed by the radiation after scattering by the product structure. Reference data (612) describes a nominal product structure. At least one synthetic image (616) of the product structure is calculated from the captured image data. Data from the synthetic image is compared with the reference data to identify defects (660-666) in the product structure. In one embodiment, a plurality of diffraction patterns are obtained using a series overlapping spots (S(1)-S(N)), and the synthetic image is calculated using the diffraction patterns and knowledge of the relative displacement. The EUV radiation may have wavelengths in the range 5 to 50 nm, close to dimensions of the structures of interest.

21 Claims, 7 Drawing Sheets

(51) Int. Cl.

| | |
|---|---|
| *G03F 1/24* | (2012.01) |
| *G03F 1/84* | (2012.01) |
| *G02B 21/36* | (2006.01) |
| *G01N 21/956* | (2006.01) |
| *G21K 7/00* | (2006.01) |
| *G01N 21/47* | (2006.01) |

(52) U.S. Cl.
CPC ......... *G02B 21/365* (2013.01); *G02B 21/367* (2013.01); *G03F 1/24* (2013.01); *G03F 1/84* (2013.01); *G21K 7/00* (2013.01); *G01N 2021/95615* (2013.01); *G01N 2201/06113* (2013.01); *G01N 2201/12* (2013.01); *G21K 2207/005* (2013.01)

(58) Field of Classification Search
USPC ................................. 355/52, 53, 55, 67–71
See application file for complete search history.

(56) References Cited

U.S. PATENT DOCUMENTS

| | | | |
|---|---|---|---|
| 8,917,393 | B2 | 12/2014 | Maiden |
| 8,942,449 | B2 | 1/2015 | Maiden |
| 9,029,745 | B2 | 5/2015 | Maiden |
| 2004/0165761 | A1 | 8/2004 | Hung et al. |
| 2006/0066855 | A1 | 3/2006 | Boef et al. |
| 2008/0069171 | A1 | 3/2008 | Rocca et al. |
| 2008/0279442 | A1 | 11/2008 | Den Boef et al. |
| 2010/0241396 | A1 | 9/2010 | Rodenburg |
| 2011/0102753 | A1 | 5/2011 | Van De Kerkhof et al. |
| 2012/0044470 | A1 | 2/2012 | Smilde et al. |
| 2012/0123748 | A1* | 5/2012 | Aben .................. G03F 7/70483 703/2 |
| 2013/0223685 | A1 | 8/2013 | Maiden |
| 2014/0268119 | A1 | 9/2014 | Chu et al. |
| 2015/0046118 | A1* | 2/2015 | Pandev .................. H01L 22/12 702/155 |
| 2015/0346605 | A1* | 12/2015 | Den Boef ............... G03F 7/705 438/401 |
| 2016/0154301 | A1 | 6/2016 | Ekinci |

FOREIGN PATENT DOCUMENTS

| | | |
|---|---|---|
| JP | 2012-117830 | 6/2012 |
| WO | WO 2014/202341 | 12/2014 |
| WO | WO 2015/095621 | 6/2015 |

OTHER PUBLICATIONS

English-Language Translation for German Patent Publication No. DE 102012022961 A1, published May 22, 2014; 40 pages.
English-Language Translation for German Patent Publication No. DE 102012022966 A1, published May 22, 2014; 27 pages.
Beckers et al., "Chemical Contrast in Soft X-Ray Ptychography," Physical Review Letters 107, 208101, American Physical Society (2011); 4 pages.
Chapman et al., "Coherent Lensless X-Ray Imaging", Nature Photonics Focus, 4, 833-839, Macmillian Publishers Limited (Dec. 2010); 7 pages.
Claus et al., "Ptychography: A novel phase retrieval technique, advantages and its application," International Conference on Applications of Optics and Photonics, Proc. of SPIE, 8001, 800109 (Jul. 2011); 6 pages.
Fujino et al., "EUV mask observations using a coherent EUV scatterometry microscope with a high-harmonic-generation source," Optomechatronic Micro/Nano Devices and Components III, Proc. of SPIE, 9658, 965818 (Jul. 2015); 8 pages.
Harada et al., "Imaging of extreme-ultraviolet mask patterns using coherent extreme-ultraviolet scatterometry microscope based on coherent diffraction imaging," Journal of Vacuum Science and Technology, 29(6), 06F503 (Nov. 2011); 7 pages.
KMLabs XUUS4 Datasheet, retrieved from http://www.kmlabs.com/content/high-harmonic-generation, 2015; 6 pages.
KMLabs Y-Fi Datasheet, retrieved from http://www.kmlabs.com/content/y-fi, 2015; 3 pages.
Lee et al., "A novel concept for actinic EUV mask review tool using a scanning lensless imaging method at the Swiss Light Source," Optomechatronic Micro/Nano Devices and Components III, Proc. of SPIE, 9048, 904811 (Apr. 2014); 7 pages.
McNulty, "Coherence and partial coherence—what do we need?", Center for Nanoscale Materials, Argonne National Laboratory, USA, at the MBA Lattice Workshop, Advanced Photon Source (Oct. 2013); 14 pages.
Miao, "Ankylography: Three-Dimensional Structure Determination from a Single View," KITP Conference on X-ray Science in the 21st Century, UCSB (Aug. 2010) (available at http://online.kitp.ucsb.edu/online/atomixrays-c10/miao/); 24 pages.
Nagata et al., "Development of highly spatial-coherent, 13.5-nm high-order harmonics for EUVL mask inspection using coherent EUV scatterometry microscope," Photonics Conference (IPC), IEEE, 935-936 (Sep. 2012); 2 pages.
"Nanoimaging: Tabletop X-Ray Coherent Diffraction Imaging at the Nano-Femto-Limits," The Kapteyn-Murnane Group, University of Colorado, 2015; 3 pages.
Osherovich et al., "Designing and using prior data in Ankylography: Recovering a 3D object from a single diffraction intensity pattern," Cornell University Library (Mar. 2012) (available at http://arxiv.org/abs/1203.4757); 2 pages.
Osherovich, "Numerical methods for phase retrieval," PhD thesis, Technion, Israel—Computer Science Department—Ph.D. Thesis, PHD-2012-04-1012 (Apr. 2012); 160 pages.
"Phase Focus: Take a Closer Look," Equity Development. Limited, London, UK (Dec. 2010) (available at www.equitydevelopment.co.uk); 27 pages.
Quiney, "Partial coherence in diffractive X-ray imaging: towards biomolecular structure determination," ARC Centre for Coherent X-ray Science, School of Physics, The University of Melbourne European XFEL Seminar, Hamburg (Feb. 2012); 56 pages.
Raines et al., "Three-Dimensional Structure Determination from a Single View," Nature, 463, 214-217, Macmillan Publishers Limited (Jan. 2010); 4 pages.
Vila-Comamala et al., "Characterization of a 20-nm hard x-ray focus by ptychographic coherent diffractive imaging," Advances in X-Ray/EUV Optics and Components VI, Proc. of SPIE, 8139, 81390.E (Sep. 2011); 7 pages.
Whitehead et al., "Diffractive Imaging Using Partially Coherent X Rays," Physical Review Letters, 103, 243902. American Physical Society (2009); 4 pages.
Wikipedia contributors, "Ewald's sphere," last modified Mar. 7, 2013, retrieved from http://en.wikipedia.org/w/index.php?title=Ewald%27s_sphere&oldid=542499752, Nov. 8, 2016; 2 pages.
Zürch et al., "Apparatus and fast method for cancer cell classification based on high harmonic coherent diffraction imaging in reflection geometry," Medical Imaging 2014: Physics of Medical Imaging, Proc. of SPIE, 9033, 903310 (Mar. 2014); 7 pages.
Zürch, "High-Resolution Extreme Ultraviolet Microscopy: Imaging of Artificial and Biological Specimens with Laser-Driven Ultrafast XUV Sources," Friedrich Schiller University of Jena, Springer Theses (2015); 139 pages.

* cited by examiner

INSPECTION APPARATUS, INSPECTION METHOD AND MANUFACTURING METHOD

BACKGROUND

Field of the Invention

The present invention relates to inspection apparatus and methods usable, for example, to perform defect detection in the manufacture of devices by lithographic techniques. The invention further relates to an illumination system for use in such inspection apparatus and to methods of manufacturing devices using lithographic techniques. The invention yet further relates to computer program products for use in implementing such methods.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Careful control and adjustment of the process is required to avoid defects such as broken lines or bridged lines. Metrology tools are used to check for defects in the applied pattern. Defect metrology is one of the most important metrology of semiconductor industry, as it deals directly with the semiconductor fab yield. Often defects are related to certain 'hot spots' on a substrate, so that metrology efforts can be concentrated on those areas. The dimensions of modern product structures are so small that they cannot be imaged by optical metrology techniques at visible wavelengths. Small features include for example those formed by multiple patterning processes, and/or pitch-multiplication. While scanning electron microscopy (SEM)_is able to resolve these modern product structures directly, SEM is much more time consuming than optical measurements.

The inventor has considered whether the techniques of coherent diffraction imaging (CDI), combined with radiation of wavelength comparable with the product structures of interest, might be applied to defect detection on modern device structures. CDI is also known as lensless imaging, because there is no need for physical lenses or mirrors to focus an image of an object. The desired image is calculated synthetically from a captured light field. Various techniques for CDI are described in the PhD thesis describing lensless imaging at EUV wavelengths is "High-Resolution Extreme Ultraviolet Microscopy" by M. W. Zürch, Springer Theses, DOI 10.1007/978-3-319-12388-2_1. A particular type of CDI is ptychography, described for example in published patent application US 2010241396 and U.S. Pat. Nos. 7,792,246, 8,908,910, 8,917,393, 8,942,449, 9,029,745 of the company Phase Focus Limited and the University of Sheffield. D. Claus et al provide an introduction to ptychography in a paper "Ptychography: a novel phase retrieval technique, advantages and its application" Proc. SPIE 8001, International Conference on Applications of Optics and Photonics, 800109 (Jul. 26, 2011); doi:10.1117/12.893512. In ptychography, phase information is retrieved from a plurality of captured images with an illumination field that is moved slightly between successive captures. Overlap between the illumination fields allows reconstruction of phase information and 3-D images. Other types of CDI can be considered also.

Another example of CDI is known as ankylography, which offers the potential to determine properties of a 3-D structure from a single capture. In order to do this, an image of a radiation field is obtained, that has been diffracted by an object, for example a microstructure made by lithography. Literature describing ankylography at EUV wavelengths includes: the paper "Designing and using prior data in Ankylography: Recovering a 3D object from a single diffraction intensity pattern" E. Osherovich et al http://arxiv.org/abs/1203.4757 and the PhD thesis by E. Osherovich "Numerical methods for phase retrieval", Technion, Israel—Computer Science Department—Ph.D. Thesis PHD-2012-04-2012). Other approaches are described in a Letter by K S Raines et al "Ankylography: Three-Dimensional Structure Determination from a Single View", published in Nature 463, 214-217 (14 Jan. 2010), doi:10.1038/nature08705 and in a related presentation by Jianwei (John) Miao, KITP Conference on X-ray Science in the 21st Century, UCSB, 2-6 Aug. 2010 (available at http://online.kitp.ucsb.edu/online/atomixrays-c10/miao/).

SUMMARY OF THE INVENTION

The present invention aims to provide an alternative inspection apparatus and method for performing inspection for defects of structures formed by lithography.

According to a first aspect of the present invention, there is provided An inspection apparatus for identifying defects in a product structure, the apparatus comprising:

a radiation source and an image detector in combination with an illumination optical system, wherein the radiation source and the illumination optical system are arranged to provide a spot of radiation on the product structure, and wherein the image detector is arranged to capture at least one diffraction pattern formed by said radiation after scattering by the product structure, and wherein the inspection apparatus further comprises a processor arranged (i) to receive image data representing said captured diffraction pattern, (ii) to receive reference data describing a nominal product structure, (iii) to calculate from the image data at least one synthetic image of the product structure, and (iv) to compare data from the synthetic image with the reference data to identify a defect in the product structure.

Such an apparatus can be used to perform so-called "lensless" imaging. This avoids the difficulties associated with providing imaging optics for the shorter wavelengths. The image obtained and used to identify defects in the structure may be called a "synthetic image" because it never existed in the physical world: it exists only as data and is obtained by computation from data representing the scattered radiation field.

The invention further provides a method of identifying defects in a product structure, the method comprising the steps:

(a) providing a spot of radiation on the product structure;

(b) capturing at least one diffraction pattern formed by said radiation after scattering by the product structure;

(c) receiving reference data describing a nominal product structure;

(d) calculating from the captured image data at least one synthetic image of the product structure; and (e) to compare data from the synthetic image with the reference data to identify a defect in the product structure.

The invention yet further provides a method of manufacturing devices wherein product structures are formed on a series of substrates by a lithographic process, wherein defects in the product structures on one or more processed substrates are measured by a method according to the invention as set forth above, and wherein the measured properties are used to adjust parameters of the lithographic process for the processing of further substrates.

The invention yet further provides a computer program product containing one or more sequences of machine-readable instructions for implementing calculating steps in a method according to the invention as set forth above.

These and other aspects and advantages of the apparatus and methods disclosed herein will be appreciated from a consideration of the following description and drawings of exemplary embodiments.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
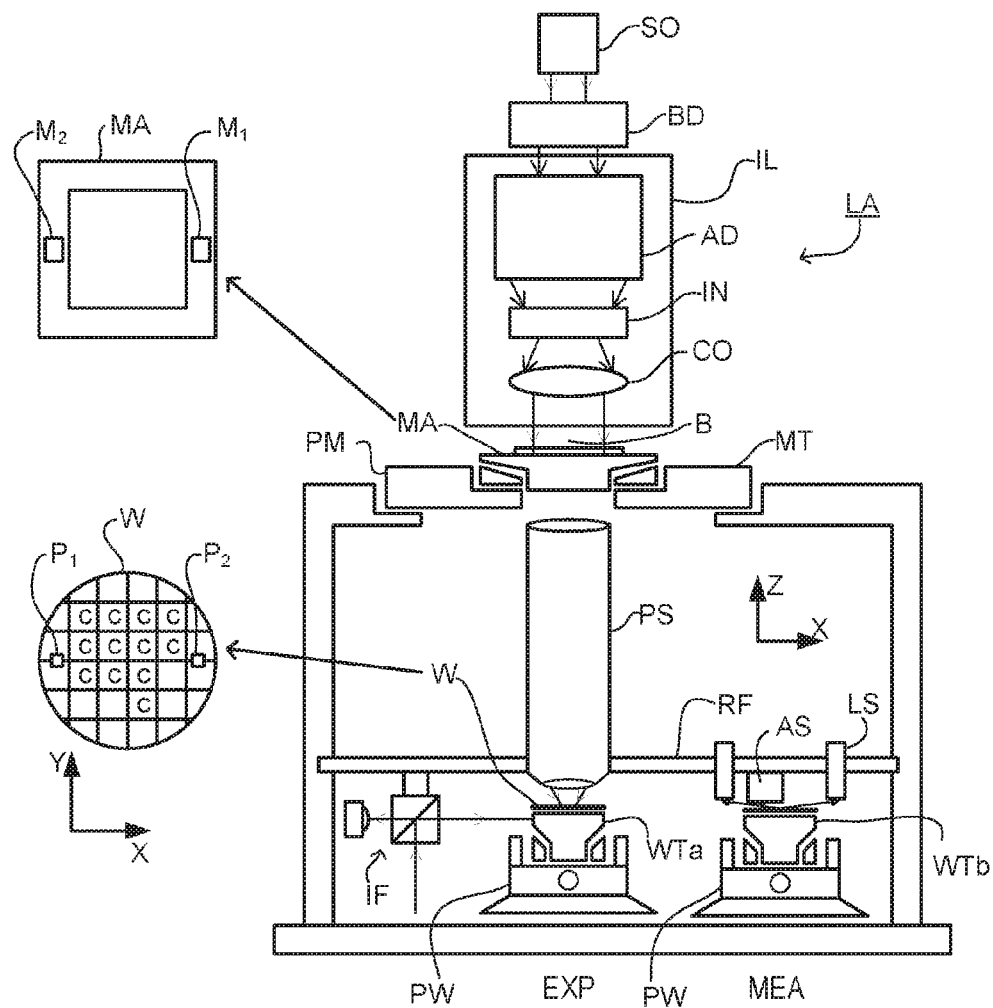
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation. For example, in an apparatus using extreme ultraviolet (EUV) radiation, reflective optical components will normally be used.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers, is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
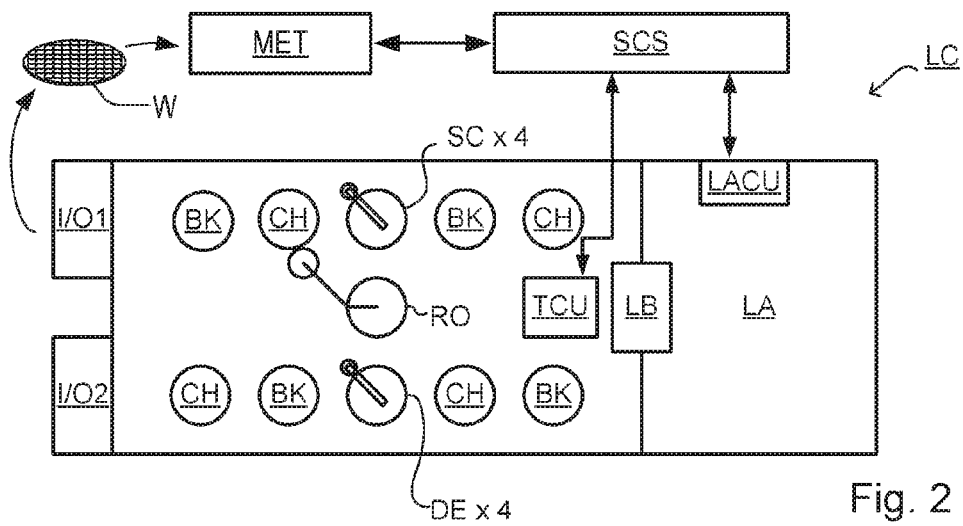
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Inspection results are provided directly or indirectly to the supervisory control system SCS.

In the remainder of the present disclosure, we are concerned particularly with inspection for defects. Within metrology system MET, an inspection apparatus is used to identify defects in the structures formed on the substrates. If errors are detected, re-working a substrate may be possible, and adjustments may be made to exposures of subsequent substrates. Metrology system MET may perform other metrology functions, using the same or different inspection apparatus.

The inspection apparatus may be integrated into the lithographic apparatus LA or the lithocell LC or may be a stand-alone device. To enable most rapid measurements, it may be desirable that the inspection apparatus measure properties in the exposed resist layer immediately after the exposure. However, not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

The inspection for defects can also be done after the resist pattern has been etched into a material beneath the resist layer. This limits the possibilities for rework of faulty substrates but can detect defects that arise in steps of the manufacturing process after the lithographic patterning.

Figure 3:
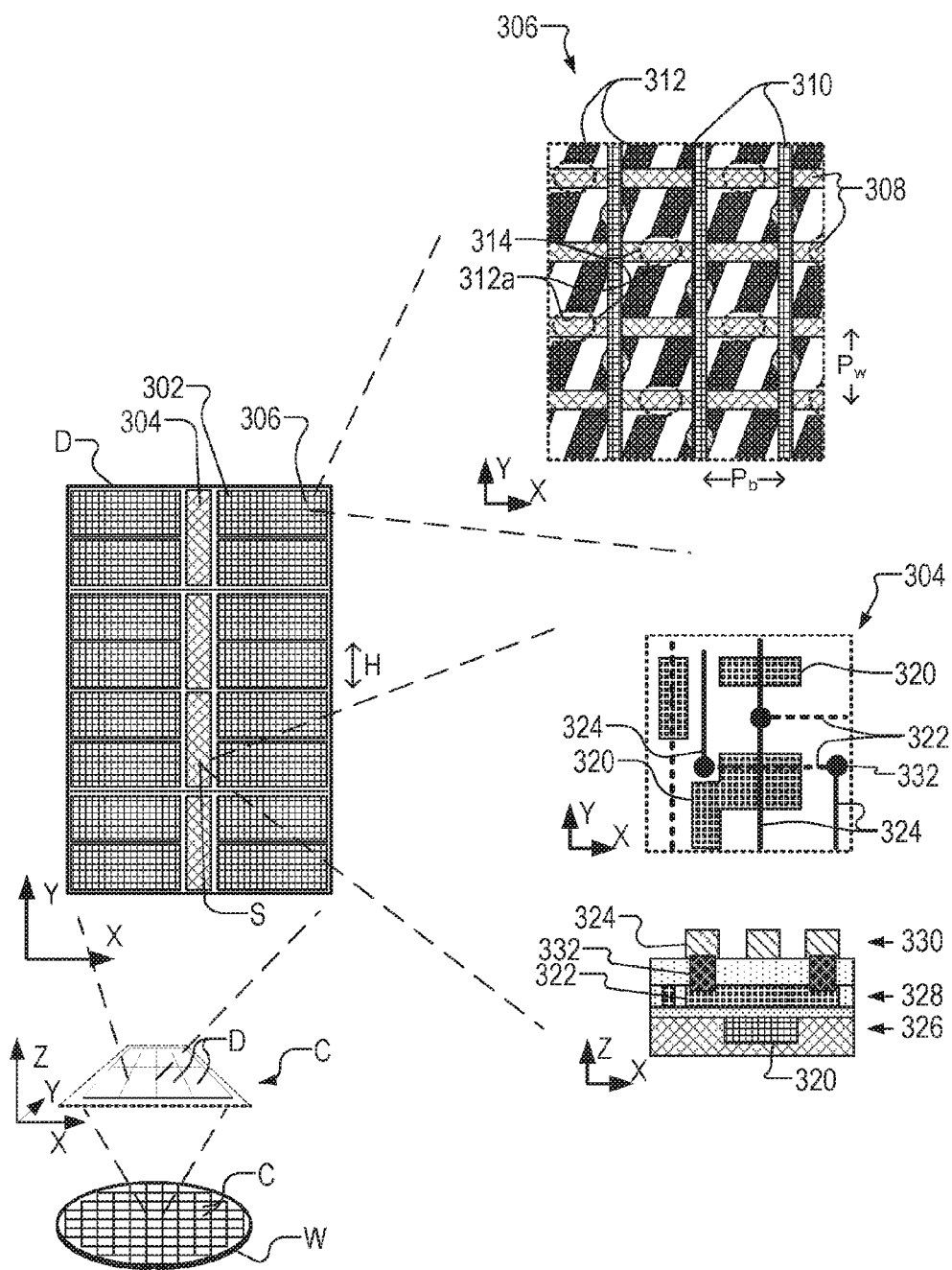
FIG. 3 illustrates schematically an example semiconductor product having areas of periodic structure and areas of non-periodic structure.

FIG. 3 illustrates characteristics of a product structure that might be subject to inspection for defects by methods of the present disclosure. It will be assumed that the product structures have been formed by optical lithography, using a system of the type described above with respect to FIGS. 1 and 2. The present disclosure is applicable to measurement of microscopic structures formed by any technique, however, not only optical lithography. A substrate W has product structure formed in target portions C, which may correspond for example to fields of the lithographic apparatus. Within each field a number of device areas D may be defined, each corresponding for example to a separate integrated circuit die.

Within each device area D, product structures formed by lithographic processing are arranged to form functional electronic components. The product illustrated may, for example, comprise a DRAM memory chip. It may have dimension of a few millimeters in each direction. The product comprises a number of memory array areas 302, and a number of logic areas 304. Within the memory array areas 302, sub-areas 306 comprise individual arrays of memory cell structures. Within these sub-areas, the product structures may be periodic. Using known reconstruction techniques, this periodicity can be exploited for measurement purposes, including defect detection On the other hand, in the logic areas 304, the structure may comprise sub-structures arranged in a non-periodic fashion. Conventional inspection techniques are not suited to such structures, and the present disclosure applies lensless imaging for example to enable defect inspection in these non-periodic areas, as well as on the periodic areas.

On the right hand side of FIG. 3, there is shown a small portion of a periodic product structure 306 (plan view only) and a small portion of non-periodic structure 304 (plan and cross-section). Again, the periodic structure could be that of a DRAM memory cell array, but this is mentioned only for the sake of example. In the example structure, conductors forming word lines 308 and bit lines 310 extend in X and Y directions throughout the periodic structure. The pitch of the word lines is marked Pw and the pitch of the bit lines is marked Pb. Each of these pitches may be a few tens of nanometers, for example. An array of active areas 312 is formed beneath the word lines and bit lines, with a slanted orientation. The active areas are formed from an array of line features, but cut at locations 312a to be divided longitudinally. The cuts may be made for example by a lithographic step using a cut mask, shown in dotted outline at 314. The process of forming the active areas 312 is thus an example of a multiple patterning process. Bit line contacts 316 are formed at locations to connect each bit line 310 with the active areas 312 below it. The skilled person will appreciate that the different types of features shown in the example product structure are separated in the Z direction, being formed in successive layers during a lithographic manufacturing process.

Also shown on the right hand side in FIG. 3 is a portion of non-periodic product structure 304, which may be part of the logic area of the DRAM product, just by way of example. This structure may comprise for example active areas 320 and conductors 322, 324. The conductors are shown only schematically in the plan view. As can be seen in the cross-section, active areas 320 are formed in a bottom layer 326, conductors 322 are formed in an intermediate layer 328 and conductors 324 are formed in a top layer 330. The term "top layer" refers to the state of manufacturing shown in the diagram, which may or may not be the top layer in a finished product. Contacts 332 are formed to interconnect conductors 322 and 324 at desired points.

Final performance of manufactured device depends critically on the accuracy of positioning and dimensioning of the various features of the product structure through lithography and other processing steps. While FIG. 3 shows the ideal or nominal product structures 304 and 306, a product structure made by a real, imperfect, lithographic process will produce a slightly different structure. The types of defects that can arise in a real product structure will be illustrated below, with reference to FIG. 4.

For defect inspection to be performed on a section of product structure in a logic area 304, a spot S of radiation is indicated. The spot diameter may be for example 10 μm or smaller. Inspection may be performed over the entire area, or only in areas known to be prone to defects (sometimes referred to as "hot spots").

Figure 4A:
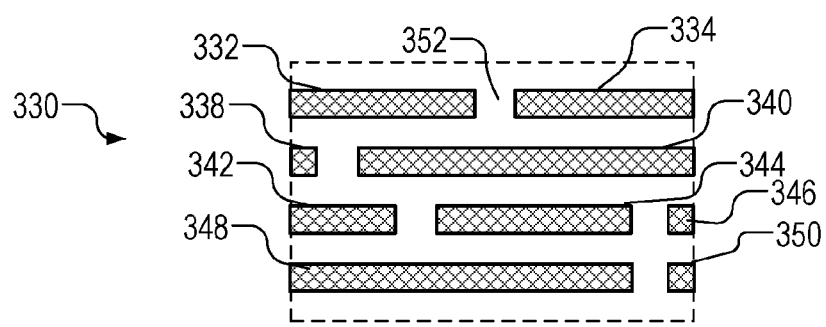
FIGS. 4(a)-4(c) illustrate a portion of a structure formed by lithography (a) in a nominal form (a) and with different types of defects (b) and (c)

FIG. 4(a) illustrates an example structure 330 that may be formed in one layer in a small area of a product. The structure comprises various features, of which some are labeled 332 to 352. Features 332-350 are for example active areas or conductors, such as may be formed in one layer within the logic area 304 shown in FIG. 3. The example illustrated may be formed by a multiple pattering process, involving successive lithographic steps. Thus, for example, features 332 and 334 have been formed by providing a line feature in one or more lithographic steps, and then forming a cut feature 352 in another lithographic step. Alternatively, this and other patterns may be formed in a single lithographic step. The illustrated features may be formed in a resist layer, for example a developed resist layer, or they may be formed in other material by deposition and etching steps subsequent to the development of the pattern in a resist layer.

Figure 4B:
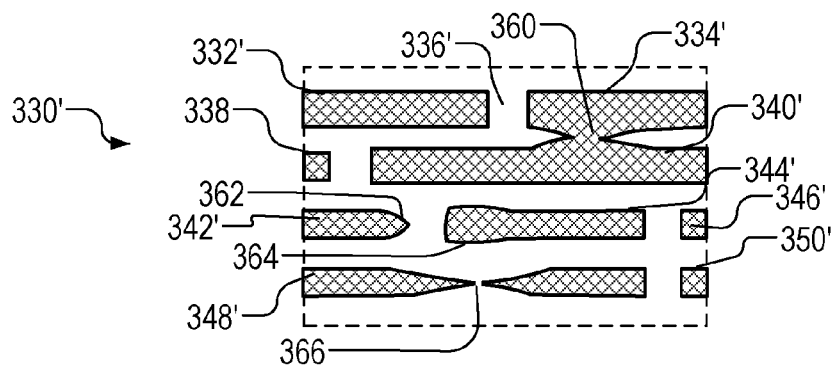

FIG. 4(a) shows the pattern of features, as it would be produced if the lithographic steps are performed with perfect alignment and perfect imaging, and any etching and other steps are also performed perfectly. Of course, as already mentioned, a real product structure produced by these steps may deviate from the form shown at (a). FIG. 4(b) shows some kinds of defect that may be present in such a real product structure The real structure is labeled 330', and the features 332 to 352 in the real structure are labeled 332' to 352' similarly. Features 334 and 340 in the real structure are somewhat thicker than in the nominal structure, and have become bridged together, indicated as a defect 360. The end of feature 342' is only partially formed (defect 362), compared to the desired features 342. An end of feature 344' is over-formed (defect 364). Feature 348' is narrower than the desired features 348, and has become undesirably interrupted (defect 366). It will be appreciated that defects 362 and 364 are of a type that may impair performance of a logic circuit in area 304, while defects 360 and 366 are of a type likely to prevent functioning altogether (yield loss).

Figure 4C:
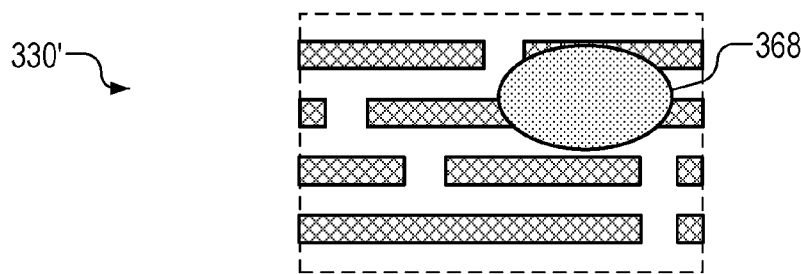

FIG. 4(c) illustrates defect 368 of another kind, namely contamination. This may be a particle of material dislodged from part of the handling apparatuses, or from the substrate or a previous substrate.

It will be appreciated that defects 362 and 364 are of a type that may impair performance of a logic circuit in area 304, while defects 360 and 366 are of a type likely to prevent functioning altogether (yield loss). Of course, these are not the only types of defects that may be present in a real product structure. Moreover, the occurrence of each type of error may vary across the substrate, and may vary within each field. Based on previous investigations and experience, it may be possible to identify some areas where defect are likely to be most severe. Inspection efforts can be directed to those areas, which may be referred to as "hot spots".

While a product in the form of a processed semiconductor substrate has been illustrated, another product requiring inspection is the mask or reticle that is used as a patterning device in the lithographic apparatus. The target structure may be part of such a patterning device. Inspection may be performed for quality control during and after manufacture of the patterning device. Inspection may be performed periodically during use of the patterning device, for example to detect damage or contamination.

The structures under inspection in the examples have patterns applied and structures formed in accordance with the patterns. However, the methods of the present disclosure can be applied also to inspection of blank substrates for semiconductor products or patterning devices. Inspection in that case can be for measurement of layer thicknesses or composition, and/or uniformity and/or for detection of defects such as damage and contamination.

Figure 5:
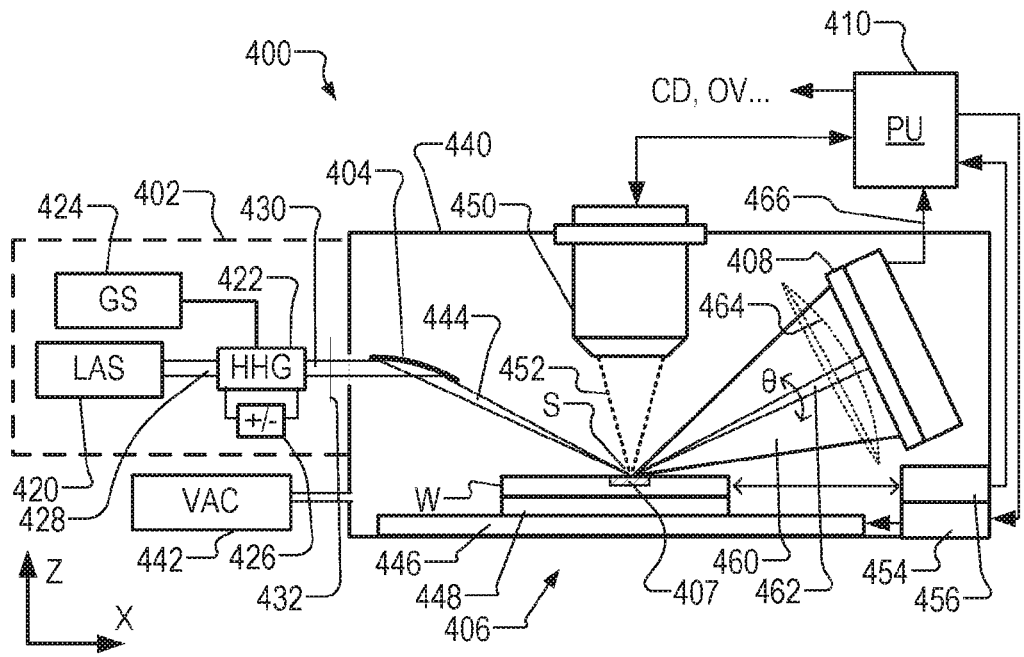
FIG. 5 illustrates schematically an inspection apparatus for use in measuring defects in a structures of the type shown in FIGS. 3 and 4.

FIG. 5 illustrates in schematic form an inspection apparatus 400 for use in the metrology system MET of FIG. 2. This apparatus is for implementing so-called lensless imaging in wavelengths in the extreme UV (EUV) and soft x-ray (SXR) ranges. The apparatus may be adapted to use hard x-rays, if desired. For the purpose of the present disclosure, hard x-rays are considered as rays with wavelength less than about 0.1 nm, for example including the range 0.01 to 0.1 nm. Soft-x-ray or EUV refers to the range extending roughly from 0.1 nm to 125 nm wavelength. Different sub-ranges of these ranges can be chosen to suit the dimensions of structures under investigation. For example, for semiconductor structures at the limits of current lithographic techniques, wavelengths in the range 0.1 to 20 nm may be considered, or 0.1 to 10 nm, or 1 to 5 nm. Not only the size of structures, but also their material properties can influence the selection of wavelengths to use in investigations. For example, to perform imaging in a reflective mode, at least background material of the structure requires good reflection strength at the wavelength used. For investigation of buried features, the wavelength should be chosen to obtain sufficient penetration through overlying material. For hard x-rays, a lower incidence angle will be required, or a transmissive mode of imaging can be adopted (not illustrated).

The inspection apparatus may be a stand-alone device or incorporated in either the lithographic apparatus LA, or the lithographic cell LC. It can also be integrated in other apparatuses of the lithographic manufacturing facility, such as an etching tool. The apparatus may of course be used in conjunction with other apparatuses such as scatterometers and SEM apparatus, as part of a larger metrology system.

Inspection apparatus 400 comprises a radiation source 402, illumination optical system 404, substrate support 406, detector 408 and processor 410. Source 402 comprises for example a generator of EUV or x-ray radiation based on high harmonic generation (HHG) techniques. Such sources are available for example from KMLabs, Boulder Co., USA (http://www.kmlabs.com/). Main components of the radiation source are a pump laser 420 and an HHG gas cell 422. A gas supply 424 supplies suitable gas to the gas cell, where it is optionally ionized by electric source 426. The pump laser may be for example a fiber-based laser with an optical amplifier, producing pulses of infrared radiation lasting less than 1 ns (1 nanosecond) per pulse, with a pulse repetition rate up to several megahertz, as required. The wavelength may be for example in the region of 1 μm (1 micron). The laser pulses are delivered as a first radiation beam 428 to the HHG gas cell 422, where a portion of the radiation is converted to higher frequencies the first radiation into a beam 430 including coherent radiation of the desired EUV or x-ray wavelength or wavelengths. For the remainder of the discussion, EUV radiation will be used as the example.

The radiation for the purpose of coherent diffraction imaging should be spatially coherent but it may contain multiple wavelengths. If the radiation is also monochromatic, the lensless imaging calculations may be simplified, but it is easier with HHG to produce radiation with several wavelengths. These are matters of design choice, and may even be selectable options within the same apparatus. Different wavelengths will, for example, provide different levels of contrast when imaging structure of different materials. For inspection of metal structures or silicon structures, for example, different wavelengths may be selected to those used for imaging features of (carbon-based) resist, or for detecting contamination of such different materials. One or more filtering devices 432 may be provided. For example a filter such as a thin membrane of Aluminum (Al) may serve to cut the fundamental IR radiation from passing further into the inspection apparatus. A grating may be provided to select one or more specific harmonic wavelengths from among those generated in the gas cell. Some or all of the beam path may be contained within a vacuum environment, bearing in mind that EUV radiation is absorbed when traveling in air. The various components of radiation source 402 and illumination optics 404 can be adjustable to implement different metrology 'recipes' within the same apparatus. For example different wavelengths and/or polarization can be made selectable.

For high-volume manufacturing applications, selection of a suitable source will be guided by cost and hardware size, not only by theoretical ability, and HHG sources are selected as the example here. Other types of sources are also available or under development that may be applied in principle. Examples are synchrotron sources, FEL (free electron laser) sources and so-called x-ray lasers. A source based on inverse Compton scattering could also be used, if developed to provide sufficient coherent radiation. Depending on the materials of the structure under inspection, different wavelengths may offer a desired level of penetration into lower layers, for imaging of buried structures. For resolving the smallest device features and defects among the smallest device features, then a short wavelength is likely to be preferred. A wavelengths in the range 1-20 nm or 1-10 nm may be chosen, for example. Wavelengths shorter than 5 nm suffer from very low critical angle when reflecting off materials typically of interest in semiconductor manufacture. Therefore to choose a wavelength greater than 5 nm will provide stronger signals at higher angles of incidence. On the other hand, if the inspection task is for detecting the presence of a certain material, for example to detect contamination, then wavelengths up to 50 nm could be useful.

From the radiation source 402, the filtered beam 430 enters an inspection chamber 440 where the substrate W including a structure of interest is held for inspection by substrate support 406. The structure of interest is labeled 407. The structure of interest may be a portion of a non-periodic product area, such as the logic area 304 of the product shown in FIG. 3. The atmosphere within inspection chamber 440 is maintained near vacuum by vacuum pump 442, so that EUV radiation can pass without undue attenuation through the atmosphere. The Illumination optics 404 has the function of focusing the radiation into a focused beam 444, and may comprise for example a two-dimensionally curved mirror, or a series of one-dimensionally curved mirrors. The focusing is performed to achieve a round or elliptical spot under 10 µm in diameter, when projected onto the structure of interest 407. Substrate support 406 comprises for example an X-Y translation stage 446 and a rotation stage 448, by which any part of the substrate W can be brought to the focal point of beam 444 to in a desired orientation. Thus the radiation spot S is formed on the structure of interest.

Tilting of the substrate in one or more dimensions may also be provided. To aid the alignment and focusing of the spot S with desired product structures, auxiliary optics 450 uses auxiliary radiation 452 under control of processor 410. Processor 410 can also communicate with a position controller 454 which operates the stages 446 and 448. Processor 410 receives highly accurate feedback on the position and orientation of the substrate, via sensors 456. Sensors 456 may include interferometers, for example, which can give accuracy in the region of picometers.

Detector 408 captures radiation 460 that is scattered by the product structure 306' over a range of angles θ in two dimensions. A specular beam 462 represents a "straight through" portion of the radiation. This specular beam may optionally be blocked by a stop (not shown), or pass through an aperture in detector 408. In a practical implementation, images with and without the central stop may be taken and combined to obtain a high dynamic range (HDR) image of a diffraction pattern. The range of angles of diffraction can be plotted on a notional sphere 464, known in the art as the Ewald sphere, while the surface of the detector 408 will more conveniently be flat. Detector 408 may be for example a CCD or CMOS image detector comprising an array of pixels.

Figure 6:
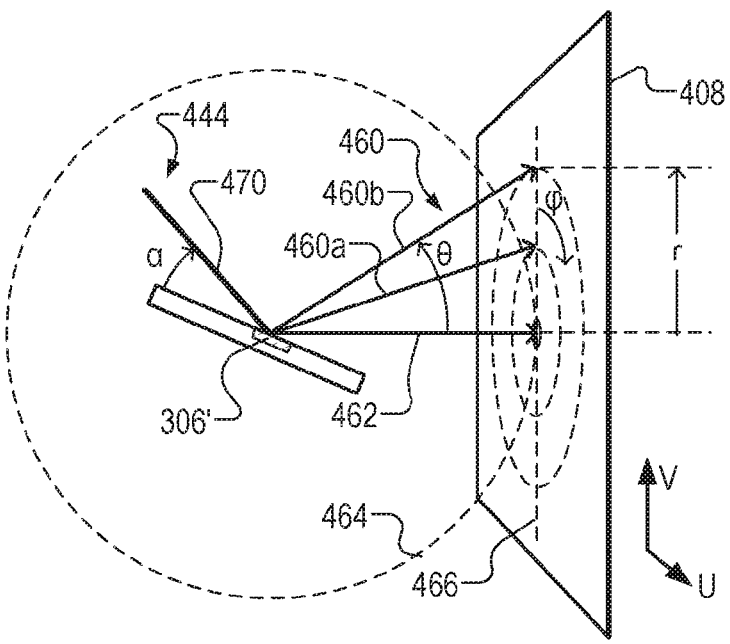
FIG. 6 (not to scale) illustrates the mapping of diffraction angles to pixels on a planar detector in the apparatus of FIG. 5.

FIG. 6 (not to scale) illustrates the mapping of diffraction angles (and consequently points on the Ewald sphere 464) to pixels on a planar detector 408. The dimensions of the pixel array are labeled U, V in a pseudo-perspective representation. The diffracted radiation 460 is deflected by a sample product structure at a point that defines the center of the Ewald sphere 464. Two rays 460a and 460b of the diffracted radiation are scattered by the product structure, with respective angles θ relative to the specular ray 462. Each ray 460a, 460b passes through a point on the (notional) Ewald sphere impinges on a particular point in the (actual) U-V plane of detector 408, where it is detected by a corresponding pixel detector. Knowing the geometry of the apparatus within the inspection chamber, processor 410 is able to map pixel positions in an image captured by detector 408 to angular positions on the Ewald sphere 462. For convenience, the specular portion 462 of the reflected radiation is aligned with the horizontal direction in the diagram, and a direction normal to the plane of detector 408. This arrangement simplifies the imaging calculations, but any coordinate system can be chosen. Thus a radial distance r on detector 408 can be mapped to an angle θ. A second angular coordinate ϕ represents deflection out of the plane of the diagram, and can be mapped also from the position on the detector. Only rays with ϕ=0 are shown in this illustration, corresponding to pixels on a line 466 on the detector.

Returning to FIG. 4, pixel data 466 is transferred from detector 408 to processor 410. Using lensless imaging, a 3-D image (model) of the target can be reconstructed from the diffraction pattern captured on the image detector. From the reconstructed image, together with knowledge of the intended pattern defects are identified by processor 410 and reported to the operator and control systems of the lithographic manufacturing facility. Note that the processor 410 could in principle be remote from the optical hardware and inspection chamber. Functions of the processor could be divided between local and remote processing units, without departing from the principles disclosed herein. For example, a local processor may control the apparatus to capture images from one or more product structures on one or more substrates, while a remote processor processes the pixel data to obtain measurements of the structure. The same processor or yet another processor could form part of the supervisory control system SCS or lithographic apparatus controller LACU and use the measurements to improve performance on future substrates.

As mentioned, the inspection apparatus is arranged to perform coherent diffraction imaging (CDI). Various techniques for CDI are described in the PhD thesis describing lensless imaging at EUV wavelengths is "High-Resolution Extreme Ultraviolet Microscopy" by M. W. Zürch, Springer Theses, DOI 10.1007/978-3-319-12388-2_1.

Referring to FIG. 7, a particular type of CDI is ptychography, described for example in published patent application US 2010241396 and U.S. Pat. Nos. 7,792,246, 8,908,910, 8,917,393, 8,942,449, 9,029,745 of the company Phase Focus Limited and the University of Sheffield. D. Claus et al provide an introduction to ptychography in a paper "Ptychography: a novel phase retrieval technique, advantages and its application" Proc. SPIE 8001, International Conference on Applications of Optics and Photonics, 800109 (Jul. 26, 2011); doi:10.1117/12.893512. In ptychography, phase information is retrieved from a plurality of captured images with an illumination field that is moved slightly between successive captures. Overlap between the illumination fields allows reconstruction of phase information and 3-D images. Other types of CDI can be considered also.

Figure 7A:
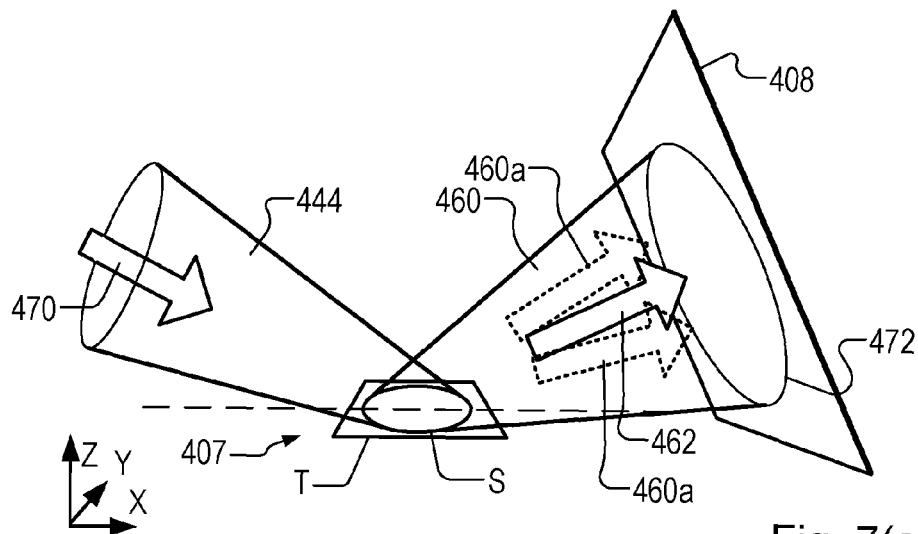
FIGS. 7(a)-7(c) illustrate illustrates obtaining of diffraction patterns from overlapping portions of a target structure for performing ptychography with the apparatus of FIG. 5.

In FIG. 7(a), we see the incident beam 444, the scattered beam 460 and the detector 408 during capture of one image of the diffraction pattern. The structure of interest 407 is represented by a square target area T. The focused spot S is at a first position, for example in the middle of the target area. Incident rays 470 are represented, specular rays 462 and scattered rays 460*a*, 460*b*, corresponding to the like-numbered rays in FIG. 6. It will be appreciated that these rays are only representative, and within the beams 444 and 460 rays are spread over a range of angles of incidence and scattering. From each point within the spot S, specular rays 462 are incident at all points within area 472 on the detector. Scattered rays 460*a*, 460*b* similarly can be incident at any point on the detector. Consequently, as explained in the Claus et al paper, diffraction orders of structures of interest within the spot S overlap with one another to form the diffraction pattern captured by detector 408. The radiation in beam 444 is spatially coherent, within the spot area S.

While full spatial coherence across the spot area would simplify calculations, it is found that partial coherence can be sufficient for good diffraction imaging, provided additional steps are applied in calculations. A survey of research in his area is provided in the presentation "Coherence and partial coherence—what do we need?" by Ian McNulty, Center for Nanoscale Materials, Argonne National Laboratory, USA, at the MBA Lattice Workshop, Advanced Photon Source, 21-22 Oct. 2013 (retrieved from the Internet 11 Aug. 2015). These and further techniques are reviewed in a presentation "Partial coherence in diffractive X-ray imaging: towards biomolecular structure determination" by Harry Quiney, ARC Centre for Coherent X-ray Science, School of Physics, The University of Melbourne (retrieved from Internet 11 Aug. 2015). In one such technique, the partially coherent radiation is modeled as superposition of a few spatially coherent modes. CDI can be performed by optimizing for each mode individually providing for these modes individually within the CDI algorithm, rather than trying to treat the radiation as coherent. This technique is described further in "Diffractive Imaging Using Partially Coherent X Rays" by L. W. Whitehead et al, Phys. Rev. Lett. 103, 243902 (2009), the contents of which are incorporated herein by reference.

Figure 7B:
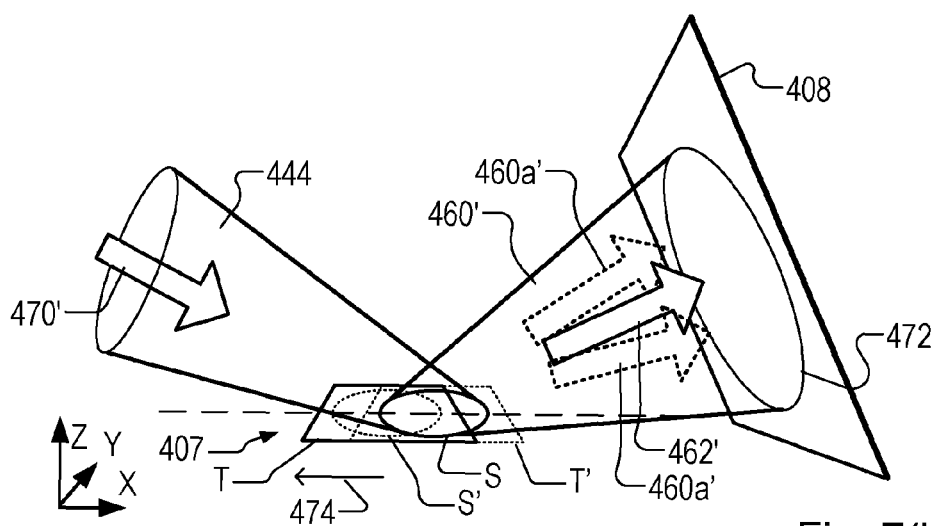

At FIG. 7(b) we see the capturing of a second diffraction pattern. At least two patterns are required for ptychography. The process is identical to that shown in FIG. 7(a). A small displacement 474 (in this illustration a translation in the X direction) has been made between the substrate and the incident beam which is now labeled 444'. As mentioned, the apparatus can record such displacement very accurately using sensors 456. Details of the displacement 474 are recorded, along with the captured diffraction patterns. In a practical implementation, adapted for use in semiconductor manufacturing, the source and other optical components will likely remain stationary, while the substrate with target area T moves to a new position using stages 446, 448 under control of processor 410. In principle, the structure of interest could remain stationary while the other components move. The spot S now falls on target area T with a spot area different from, but significantly overlapping the former position S'. The former position of target area T is shown as T'. Scattered rays 460*a*', 460*b*' are captured on detector 408 as before. The diffraction pattern, which records only intensity, may be very similar to that captured in FIG. 7(a), but slight differences between the patterns can be used to reconstruct phase information, thanks to the overlapping of the spot areas S and S'. The degree of overlap between adjacent spot areas may be greater than 30%, for example around 50% of the spot area.

Figure 7C:
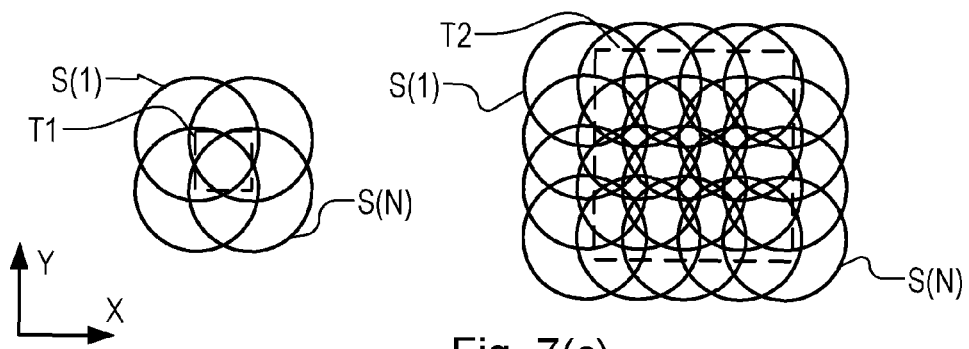

More than two diffraction patterns may be captured, as required. FIG. 7(c) shows two examples where a target areas T1 and T2 are each covered by a series of displaced radiation spots S(1) to S(N), all mutually displaced in X and/or Y directions but all overlapping significantly one or more of their neighbors. Bearing in mind that even though the spot S is only 5 or 10 μm in diameter, the resolution of imaging desired is on the order of 1 nm. The area that is covered by the calculated image corresponds to those areas where at least two spots overlap, so the rectangular areas T1, T2 could in principle be extended into a more complex shape if desired. Nevertheless, it will be appreciated that the synthesized image might cover a target area T1 that is only for example 2 μm by 2 μm, in the case of area T1. Even so, it may encompass many hundreds or even thousands of functional devices within a product such as the DRAM chip of FIG. 3. Consequently, only two or a few captures may be required in a practical inspection task.

The inventor has determined that coherent diffraction imaging, for example ptychography can be applied to the inspection of complex, extensive device structures. The described techniques use radiations of wavelength comparable with the smallest features made by modern semiconductor lithographic technique to achieve defect inspection with a high spatial resolution. The brightness of an HHG radiation source (and alternative future sources such as coherent inverse Compton scattering sources) enables measurements to be performed in a fraction of a second, as required for regular inspection during high volume manufacture. Using CDI a high resolution image of the actual structure can be obtained, which can then be compared with the nominal structure to identify defects of the type illustrated in FIG. 4.

Figure 8:
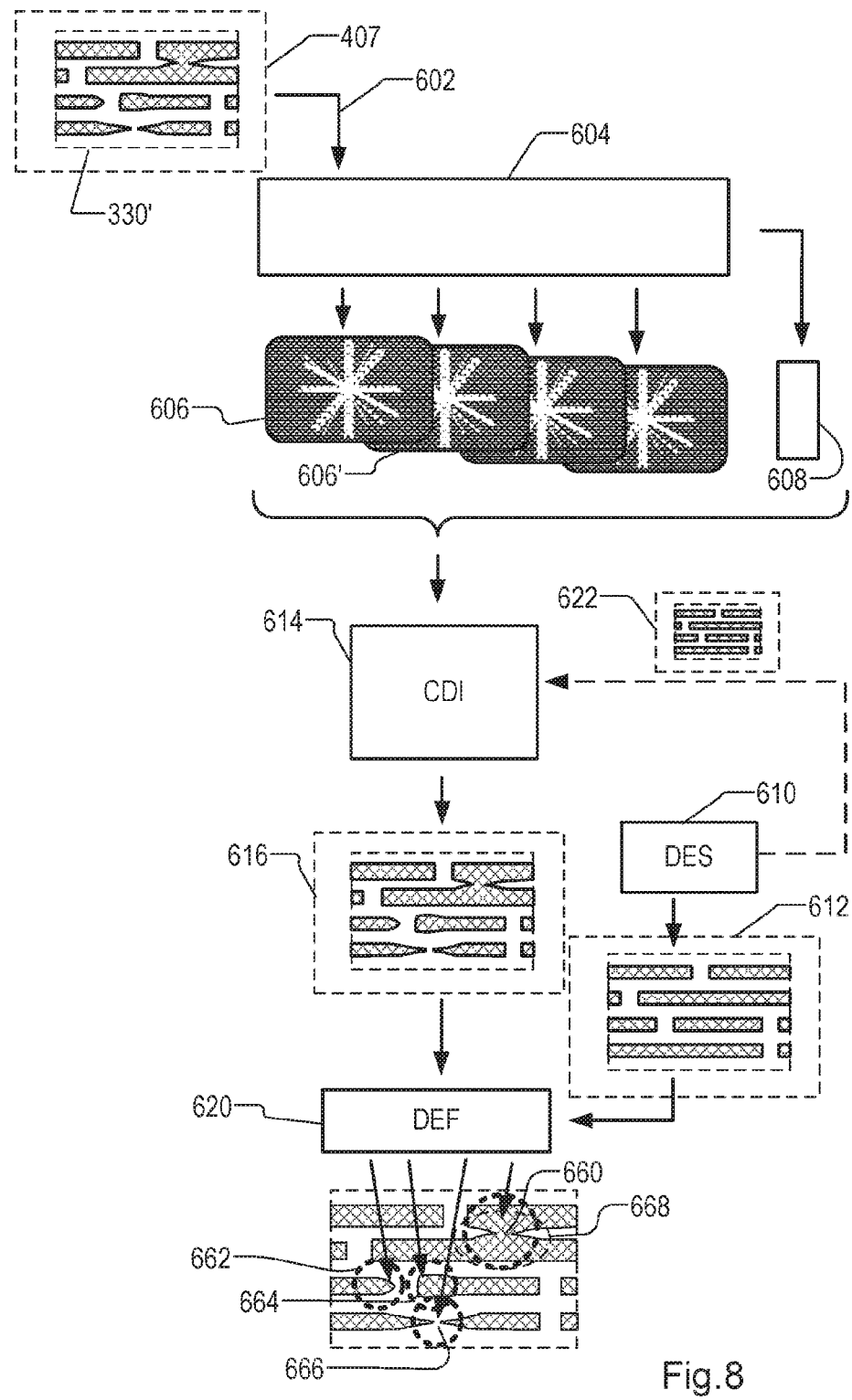
FIG. 8 illustrates schematically a method of inspecting a structure of interest according to an embodiment of the invention, using for example the method of ptychography in the apparatus of FIG. 5.

FIG. 8 illustrates the complete defect inspection process using the apparatus of FIG. 5 to measure properties of the structure of interest 407. The process is implemented by operation of the hardware illustrated in the drawings, in conjunction with processor 410 operating under control of suitable software (program instructions). As mentioned above functions of (i) controlling the operations of the hardware and (ii) processing the image data 466 may be performed in the same processor, or may be divided between different dedicated processors. Processing of the image data need not even be performed in the same apparatus or even in the same country.

At 602 a product structure 407 is presented to the radiation spot S in inspection chamber 440, using actuators of substrate support 406. This structure of interest may for example include the product structure 330' illustrated in FIG. 4(*b*) or (*c*), which in turn may be a small area within logic area 304 of the product illustrated in FIG. 3. Radiation source 402 and detector 408 are operated one or more times at 604 to capture at least one intensity distribution image 606 recording a diffraction pattern when the spot S is irradiating the structure of interest in a first relative position. For an embodiment using ptychography, two or more images may be captured, with shifted but overlapping spots S, in the overlapping manner illustrated in FIG. 7. Thus, one or more additional images 606' are obtained to capture respective diffraction patterns. Where the radiation source produces thousands of pulses per second of EUV radiation, a single captured image may for example accumulate photons from many pulses. A single image 606, 606' etc. may also be synthesized from several individual captures, for example for noise reduction and/or high dynamic range (HDR) purposes. These details will be understood to underlie the simplified version of the process presented here. Also recorded is auxiliary data (metadata) 608 defining operating parameters of the apparatus associated with each image, for example the illumination wavelength, polarization and the like. This metadata may be received with each image 606, 606', or defined and stored in advance for a set of images. Importantly for ptychography, auxiliary data 608 records the relative displacements 474 that allow the positions of the spots to be related to one another, between the images.

Also received or previously stored is reference data from a database 610. In the present example, reference data 612 represents at least some features of the nominal structure 330 to which the real device structure 330' is supposed to conform. The reference data may for example comprise a parameterized description of the nominal structure. It may for example comprise the path, line width, line height of every feature in a layer. It may comprise a parameterized description of more than one layer. It may comprise an actual image of a good example product.

From the received image data 606, 606' and the metadata 608 and the reference data 612, processor PU performs coherent diffractive imaging calculations at 614. These include for example iterative simulations of interaction between radiation and a structure, using the knowledge of the overlapping spot areas S, S' to constrain the simulations. Using this knowledge, phase retrieval can be achieved, even though each captured image by itself is only an intensity of the diffraction pattern. The calculations at step 614 can be performed for example to calculate a synthetic 2-dimensional or 3-dimensional image 616 of the real product structure as it would be seen if focused by real imaging optical system onto an image sensor.

Detailed implementation of the step 614 can be based on the techniques of lensless imaging disclosed in the Phase Focus/Sheffield University references above. Although the representations of the image 616 and reference data 612 are two-dimensional in the present drawings, it will be understood that the method can produce three-dimensional images, or two-dimensional images focused to different depths, so that the features in different layers of the product structure can be resolved. For many defect inspection purposes, a two-dimensional image will be sufficient.

At 620 calculations are made to compare the reconstructed image 616 with the nominal structure 612 and thereby detect defects in the real structure. Using the example features within structure 330', image 616 shows these at 330''. These features are compared those of the nominal structure 330 represented in the reference data 612 to identify and report defects 660, 662, 664, 666 that correspond to the defects 360, 362, 364 and 366 in the real structure 330'. In the case of contamination defect 368 (FIG. 4(c)), this would also be detected as illustrated at 668.

Defects can be detected in a number of ways, without departing from the basic method described here. For example, image 616 can be compared as a whole with an expected image representing in the reference data 612. Alternatively, individual features can be identified and compared with corresponding features represented in the reference data 612.

As illustrated in broken lines at, reference data 622 from database 610 may be used in the CDI process 614. The manner in which such data may be useful depends on the form of CDI and the challenges of a particular situation. As one example, in known iterative phase retrieval techniques described for example in the Zürch reference, an initialization phase assigns random phase to pixels of the captured diffraction patterns. Instead of assigning random phases, reference data 622 representing the expected structure can be used to calculate a simulated diffraction pattern, including phase information, by a forward diffraction model. This simulated phase information can be used as the initial phase estimate in the iterative phase retrieval process. In this way, the iterative process may be expected to converge more quickly and/or more reliably to the correct values for the real structure. Use of this reference data 622 may also reduce the number of captured images required for CDI to succeed, or relax image noise constraints. Either of these benefits will help to reduce overall acquisition time, allowing greater throughput of structures, or a greater number of inspections.

The illustrated process is repeated for all structures of interest, which may be spaced through a device area 304, 306, and/or across a substrate W. Note that the computational parts of the process can be separated in time and space from the image capture. The computations do not need to be completed in real time, although of course that would be desirable. Only the capturing of the images at 604 requires the presence of the substrate, and so only that step impacts productivity throughput of the lithographic manufacturing process overall.

The principle behind CDI processes is to use redundancy of information in a Fourier space of the structure of interest. In ptychography, this redundancy is obtained using overlapping spots of radiation with a translation between captures is conventionally used. CDI can be performed with different types of redundancy if preferred. For example, an information pattern (coding) can be superimposed on the incident radiation, to assist phase retrieval. Different techniques can be used in combination or as alternatives. in another variation, diffraction patterns can be captured using different wavelengths, instead of or in addition to displacement of the spot. The image data for different wavelengths can be used in a single CDI calculation, or separate CDI calculations could be performed to obtain different synthetic images of the same structure of interest. These different synthetic images can be used together, or a best one selected.

As mentioned above, using x-rays shorter than 0.1 nm in wavelength may require a change of geometry of the apparatus. A shallower grazing incidence angle $\alpha$ may be used, or a transmission mode may be used instead. Using hard x-rays in grazing incidence, it is difficult to control the spot size in at least one dimension, because of the extremely shallow incidence angle that is required to get a useful reflectivity. However, if the source power allows it, the technique can work with higher angle of incidence, to keep the spot size small. An advantage of using EUV radiation in the range 1-20 nm or 1-40 nm, for example, is that, compared with shorter x-ray wavelengths, substantial reflectance can be obtained from typical product materials, at angles $\alpha$ greater than 5°, or even greater than 10° or greater than 20°. Coupled with a bright source such as an HHG source or inverse Compton scattering source, a high throughput of inspections can be achieved with a small radiation spot. Where the source is bright enough, lower reflectances can be tolerated, allowing normal or near-normal incidence to be used.

A method of manufacturing devices using the lithographic process can be improved by providing an inspection apparatus as disclosed herein, using it to inspect processed substrates to identify defects in one or more structures of interest, and adjusting parameters of the process to improve or maintain performance of the lithographic process for the processing of subsequent substrates.

Figure 9:
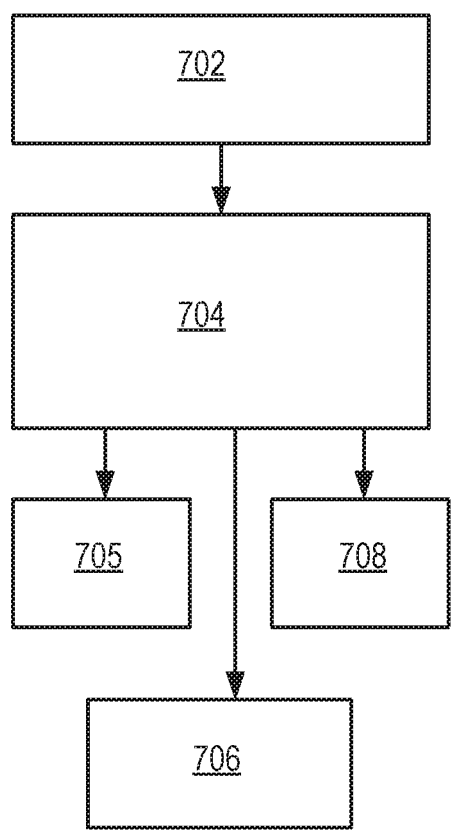
FIG. 9 illustrates use of the method of FIG. 7 in controlling a lithographic manufacturing process.

FIG. 9 illustrates a general method of controlling a lithographic manufacturing facility such as the one shown in FIGS. 1 and 2, using the lensless imaging methods described above. At 702, a substrate is processed in the facility to produce one or more structures 407 on a substrate such as a semiconductor wafer. The structures may be distributed at different locations across the wafer. The structures may be parts of functional devices, or they may be dedicated metrology targets. At 704 the method of FIG. 7 is used to identify defects in the structures 407 at locations across the wafer. At 705, if appropriate, remedial action such as re-work, and/or cleaning of a substrate or part of an apparatus is instructed based on the detection of defects. At 706 recipes for controlling the lithographic apparatus and/or other processing apparatuses are updated based on the defects reported in step 704. For example, the updates may be designed to correct deviations from ideal imaging performance, or from ideal etching performance, identified by the lensless imaging. At 708, optionally, the recipe for performing the inspection on future substrates, or recipes for other metrology operations may be revised based on findings in step 704 or from elsewhere.

By the techniques disclosed herein, imaging at high resolution can be performed on real product structures. Comparing with prior knowledge of the nominal structure allows defects to be identified. Prior knowledge may also be used to improve phase retrieval. This may help to reduce the acquisition time and so aid high-volume measurement in high-volume manufacturing context.

In association with the optical system hardware, an implementation of the inspection methods and inspection apparatus disclosed herein may include a computer program containing one or more sequences of machine-readable instructions defining methods of calculating synthetic images and/or controlling the inspection apparatus 400 to implement the illumination modes and other aspects of those metrology recipes. This computer program may be executed for example in a separate computer system employed for the image calculation/control process. Alternatively, the calculation steps may be wholly or partly performed within unit PU in the apparatus of FIG. 5 and/or the control unit LACU and/or the supervisory control system SCS of FIGS. 1 and 2. There may also be provided a data storage medium (e.g., semiconductor memory, magnetic or optical disk) having such a computer program stored therein.

Further embodiments according to the current invention are provided in below numbered clauses:

1. An inspection apparatus for identifying defects in a product structure, the apparatus comprising a radiation source and an image detector in combination with an illumination optical system, wherein the radiation source and the illumination optical system are arranged to provide a spot of radiation on the product structure, and wherein the image detector is arranged to capture at least one diffraction pattern formed by said radiation after scattering by the product structure, and wherein the inspection apparatus further comprises a processor arranged (i) to receive image data representing said captured diffraction pattern, (ii) to receive reference data describing a nominal product structure, (iii) to calculate from the image data at least one synthetic image of the product structure and (iv) to compare data from the synthetic image with the reference data to identify a defect in the product structure.

2. An inspection apparatus according to clause 1 wherein the apparatus is arranged to obtain a plurality of diffraction patterns using a series of two or more spots of radiation displaced from one another but overlapping one another, and said processor is arranged to calculate said synthetic image using said two or more diffraction patterns and using knowledge of the relative displacement of the spots to perform phase retrieval.

3. An inspection apparatus according to clause 2 wherein said reference data is used to assist in calculation of the synthetic image.

4. An inspection apparatus according to clause 3 wherein said reference data is used to calculate an initial phase estimate corresponding to the captured diffraction pattern.

5. An inspection apparatus according to any preceding clause wherein said reference data is an image of a nominal structure and the synthetic image is compared with the image of the nominal structure to identify said defect.

6. An inspection apparatus according to any preceding clause wherein said radiation source comprises a higher harmonic generator and a pump laser.

7. An inspection apparatus according to any preceding clause including a wavelength selector for selecting a wavelength of said radiation.

8. An inspection apparatus according to any preceding clause wherein the radiation source and the illumination optical system are arranged to provide the radiation having a wavelength less than 50 nm.

9. An inspection apparatus according to any preceding clause wherein said illumination optical system is operable to deliver said spot of radiation with a diameter less than 15 µm.

10. An inspection apparatus according to any preceding clause arranged to process automatically a series of product structures that have been formed on a semiconductor substrate.

11. A method of identifying defects in a product structure, the method comprising the steps:

(a) providing a spot of radiation on the product structure;

(b) capturing at least one diffraction pattern formed by said radiation after scattering by the product structure;

(c) receiving reference data describing a nominal product structure;

(d) calculating from the captured image data at least one synthetic image of the product structure; and (e) to compare data from the synthetic image with the reference data to identify a defect in the product structure.

12. A method according to clause 11 wherein steps (a) and (b) are repeated to obtain a plurality of diffraction patterns using a series of two or more spots of radiation displaced from one another but overlapping one another, and in step (d) said synthetic image is calculated using said two or more diffraction patterns and using knowledge of the relative displacement of the spots to perform phase retrieval.

13. A method according to clause 12 wherein said reference data is used to assist in calculation of the synthetic image.

14. A method according to clause 13 wherein said reference data is used to calculate an initial phase estimate corresponding to the captured diffraction pattern.

15. A method according to any of clauses 11 to 14 wherein said reference data is an image of a nominal structure and in step (e) the synthetic image is compared with the image of the nominal structure to identify said defect.

16. A method according to any of clauses 11 to 15 wherein said radiation is generated by a source comprising a higher harmonic generator and a pump laser.

17. A method according to any of clauses 11 to 16 including selecting a wavelength of the provided radiation from a range of wavelengths generated by the source.

18. A method according to any of clauses 11 to 17 wherein the provided radiation has a wavelength less than 50 nm.

19. A method according to any of clauses 11 to 18 wherein said spot of radiation has a diameter less than 15 μm.

20. A method of manufacturing devices wherein device features and metrology targets are formed on a series of substrates by a lithographic process, wherein defects on one or more processed substrates are identified by a method according to any of clauses 11 to 19, and wherein the identification of one or more a defects is used to adjust parameters of the lithographic process for the processing of further substrates.

21. A method of manufacturing devices wherein device features and metrology targets are formed on a series of substrates by a lithographic process, wherein defects on one or more processed substrates are identified by a method according to any of clauses 11 to 19, and wherein the identification of one or more a defects is used to trigger an intervention in the handling of the substrate having the identified defect.

22. A computer program product containing one or more sequences of machine-readable instructions for implementing the calculating step of a method of any of clauses 11 to 19.

23. A computer program product containing one or more sequences of machine-readable instructions for causing a processing device to implement the processor the inspection apparatus of any of clauses 1 to 10.

Although specific reference may have been made above to the use of embodiments of the invention in the context of optical lithography, it will be appreciated that the invention may be used in other applications, for example imprint lithography. In imprint lithography, topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An inspection apparatus for identifying a defect in a product structure, the apparatus comprising:
   an illumination optical system configured to provide a spot of radiation on the product structure;
   an image detector configured to capture a diffraction pattern formed by the spot of radiation scattering by the product structure; and
   a processor configured to:
      receive image data representing the captured diffraction pattern,
      receive reference data describing a nominal product structure,
      calculate, from the image data, a synthetic image of the product structure, and
      compare data from the synthetic image with the reference data to identify the defect in the product structure.

2. The inspection apparatus of claim 1, wherein:
   the inspection apparatus is configured to obtain a plurality of diffraction patterns using a series of two or more spots of radiation displaced from one another but overlapping one another, and
   the processor is configured to calculate the synthetic image using the plurality of diffraction patterns and to use a relative displacement of the two or more spots of radiation to perform phase retrieval.

3. The inspection apparatus of claim 2, wherein the processor is further configured to use the reference data in the calculating the synthetic image.

4. The inspection apparatus of claim 3, wherein the processor is further configured to use the reference data to calculate an initial phase estimate corresponding to the captured diffraction pattern.

5. The inspection apparatus of claim 1, wherein:
   the reference data is an image of the nominal product structure; and
   the synthetic image is compared with the image of the nominal structure to identify the defect.

6. The inspection apparatus of claim 1, further comprising a radiation source comprising a high harmonic generator and a pump laser.

7. The inspection apparatus of claim 1, further comprising a wavelength selector for selecting a wavelength of the radiation.

8. The inspection apparatus of claim 1, further comprising a radiation source, wherein the radiation source and the illumination optical system are configured to provide the radiation having a wavelength less than 125 nm.

9. The inspection apparatus of claim 1, wherein the illumination optical system is configured to deliver the spot of radiation with a diameter less than 15 μm.

10. The inspection apparatus of claim 1, wherein the inspection apparatus is configured to process automatically a series of product structures that have been formed on a semiconductor substrate.

11. A method of identifying a defect in a product structure, the method comprising:
   providing radiation on the product structure;
   capturing a diffraction pattern formed by the radiation scattering by the product structure;
   receiving image data representing the captured diffraction pattern;
   receiving reference data describing a nominal product structure;
   calculating, from the image data, a synthetic image of the product structure; and comparing data from the synthetic image with the reference data to identify a defect in the product structure.

12. The method of in claim 11, further comprising:
repeating the providing and the capturing to obtain a plurality of diffraction patterns using a series of two or more spots of radiation displaced from one another but overlapping one another;
using the plurality of diffraction patterns to calculate the synthetic image; and
using a relative displacement of the spots to perform phase retrieval.

13. The method of claim 12, further comprising using the reference data in the calculating the synthetic image.

14. The method of claim 13, further comprising using the reference data to calculates an initial phase estimate corresponding to the captured diffraction pattern.

15. The method of claim 11, wherein:
the reference data is an image of the nominal structure; and
the calculating comprises comparing the synthetic image with the image of the nominal structure to identify the defect.

16. The method of claim 11, further comprising selecting a wavelength of the provided radiation from a range of wavelengths generated by a radiation source.

17. A method of manufacturing devices, comprising:
forming device features and metrology targets on a series of substrates by a lithographic process;
identifying defects on one or more processed substrates by:
providing a spot of radiation on the device features or the metrology targets;
capturing a diffraction pattern formed by the spot of radiation scattering by the device features or the metrology targets;
receiving reference data describing nominal device features or nominal metrology targets;
calculating from the captured diffraction pattern a synthetic image of the device features or metrology targets; and
comparing data from the synthetic image with the reference data to identify a defect in the device features or the metrology targets; and
adjusting parameters of the lithographic process for processing of further substrates based on the identified defect.

18. A non-transitory computer program product comprising machine-readable instructions for causing a processor to perform operations comprising:
providing a spot of radiation on a product structure;
capturing a diffraction pattern formed by the spot of radiation scattering by the product structure;
receiving reference data describing a nominal product structure;
calculating, from the captured diffraction pattern, a synthetic image of the product structure; and
comparing data from the synthetic image with the reference data to identify a defect in the product structure.

19. A method of manufacturing devices, comprising:
forming device features and metrology targets on a series of substrates by a lithographic process,
identifying defects on one or more processed substrates by:
providing a spot of radiation on the device features or the metrology targets;
capturing at least one diffraction pattern formed by the spot of radiation scattering by the device features or the metrology targets;
receiving reference data describing nominal device features or nominal metrology targets;
calculating, from the captured diffraction pattern, a synthetic image of the device features or the metrology targets; and
comparing data from the synthetic image with the reference data to identify a defect in the device features or the metrology targets, and
trigger an intervention in handling of the substrate having the identified defect based on the identifying defects.

20. The inspection apparatus of claim 1, wherein the processor is further configured to use auxiliary data associated with the radiation in the calculating the synthetic image.

21. The inspection apparatus of claim 1, further comprising a radiation source, wherein the radiation source and the illumination optical system are configured to provide the radiation having a wavelength less than 50 nm.

* * * * *

UNITED STATES PATENT AND TRADEMARK OFFICE
CERTIFICATE OF CORRECTION

| | |
|---|---|
| PATENT NO. | : 9,823,586 B2 |
| APPLICATION NO. | : 15/230937 |
| DATED | : November 21, 2017 |
| INVENTOR(S) | : Richard Quintanilha |

It is certified that error appears in the above-identified patent and that said Letters Patent is hereby corrected as shown below:

In the Claims

In Column 21, Line 15, Claim 14, please delete "calculates" and insert --calculate--.
In Column 22, Line 35, Claim 19, please delete "defects" and insert --defect--.

Signed and Sealed this
Sixth Day of March, 2018

Andrei Iancu
*Director of the United States Patent and Trademark Office*